United States Patent
Kisak et al.

(10) Patent No.: US 7,795,309 B2
(45) Date of Patent: Sep. 14, 2010

(54) TOPICAL FORMULATION INCLUDING DICLOFENAC, OR A PHARMACEUTICALLY ACCEPTABLE SALT THEREOF

(75) Inventors: Edward T. Kisak, La Jolla, CA (US); John M. Newsam, San Diego, CA (US); Dominic King-Smith, San Diego, CA (US); Pankaj Karande, Boston, MA (US); Samir Mitragotri, Goleta, CA (US)

(73) Assignee: FQUBED Inc., San Diego, CA (US)

( * ) Notice: Subject to any disclaimer, the term of this patent is extended or adjusted under 35 U.S.C. 154(b) by 0 days.

(21) Appl. No.: 12/281,561

(22) PCT Filed: Mar. 6, 2007

(86) PCT No.: PCT/IB2007/001983

§ 371 (c)(1),
(2), (4) Date: Jan. 12, 2009

(87) PCT Pub. No.: WO2007/102090

PCT Pub. Date: Sep. 13, 2007

(65) Prior Publication Data

US 2010/0029769 A1    Feb. 4, 2010

Related U.S. Application Data

(60) Provisional application No. 60/778,847, filed on Mar. 6, 2006.

(51) Int. Cl.
*A61K 31/195* (2006.01)

(52) U.S. Cl. ..................................................... 514/561
(58) Field of Classification Search .................. 514/561
See application file for complete search history.

(56) References Cited

U.S. PATENT DOCUMENTS

| | | | | |
|---|---|---|---|---|
| 5,602,183 | A | * | 2/1997 | Martin et al. ............... 514/724 |
| 5,648,380 | A | * | 7/1997 | Martin ....................... 514/461 |
| 5,874,479 | A | * | 2/1999 | Martin ....................... 514/724 |
| 6,328,979 | B1 | | 12/2001 | Yamashita et al. |
| 7,001,592 | B1 | | 2/2006 | Traynor et al. |
| 2002/0064524 | A1 | * | 5/2002 | Cevc ....................... 424/94.63 |

FOREIGN PATENT DOCUMENTS

| | | |
|---|---|---|
| WO | 2005009510 A2 | 2/2005 |
| WO | 2007/102090 A3 | 9/2007 |

OTHER PUBLICATIONS

Written Opinion of the International Searching Authority of International Application No. PCT/IB07/01983; mailed on Aug. 8, 2008.

* cited by examiner

*Primary Examiner*—Raymond J Henley, III
(74) *Attorney, Agent, or Firm*—Katten Muchin Rosenman LLP

(57) ABSTRACT

There is described a topical formulation. The topical formulation comprises: (i) diclofenac or a pharmaceutically acceptable salt thereof, (ii) a first compound, and (iii) a second compound. The first compound and second compound are different, and each is selected from the group consisting essentially of N-lauroyl sarcosine, sodium octyl sulfate, methyl laurate, isopropyl myristate, oleic acid, glyceryl oleate and sodium lauryl sulfoacetate. It has been discovered that certain combination of compounds are excellent penetration enhancers and, as such, can be incorporated in a topical formulation to facilitate administration of diclofenac or a pharmaceutically acceptable salt thereof. The increased penetration enhancement can also lead to a reduction in the total concentration of skin irritants in the formulation.

33 Claims, No Drawings

TOPICAL FORMULATION INCLUDING DICLOFENAC, OR A PHARMACEUTICALLY ACCEPTABLE SALT THEREOF

This application is a national stage of PCT/IB2007/001983, filed on Mar. 6, 2007, which claims priority to U.S. Provisional Application No. 60/778,847, filed on Mar. 6, 2006.

FIELD OF THE INVENTION

The present invention relates to a topical formulation of multiplexed molecular penetration enhancers. More particularly, the present invention relates to a topical formulation of multiplexed molecular penetration enhancers for topical or transdermal administration of diclofenac or a pharmaceutically acceptable salt thereof.

DESCRIPTION OF THE PRIOR ART

Topical formulations for application to the skin can be useful in cosmetic applications, for treating conditions of the upper skin layers and for transdermal administration of active agents to the local tissue underlying the skin or into the blood for systemic distribution. Use of a topical formulation of, for instance, a pharmaceutical agent is advantageous in that it avoids first-pass metabolism, circumvents gastrointestinal ("GI") absorption, can allow delivery of an active ingredient with a relatively short biological half-life and/or a narrow therapeutic window and facilitates uniform plasma dosing of the active ingredient, and/or can improve user compliance.

In spite of the advantages, transdermal administration is currently limited to about a dozen small lipophilic drugs, available in transdermal patch format (including scopolamine, fentanyl, estradiol, nitroglycerine, nicotine and testosterone).

Skin has evolved to impede the flux of exogenous molecules so as to provide a strong barrier to molecular delivery, particularly agents such as pharmaceutical agents. Transdermal drug administration is difficult since skin is an excellent diffusion barrier.

Structurally, the skin consists of two principle parts: (i) a relatively thin outermost layer (the 'epidermis'), and (ii) a thicker inner region (the 'dermis'). The outermost layer of the epidermis (the 'stratum corneum') consists of flattened dead cells which are filled with keratin. The region between the flattened dead cells of the stratum corneum are filled with lipids which form lamellar phases. The highly impermeable nature of skin is due primarily to the stratum corneum. The viable epidermis underlying the stratum corneum is akin to other living tissue. The dermis provides the skin's structural strength as well as the nerve and vascular networks that support the epidermis.

Delivering an active agent into or through the skin in sufficient concentrations often requires some means for reducing the stratum corneum's hindrance of penetration. A number of methods for lowering the stratum corneum's barrier properties have been developed including electrically assisted techniques such as iontophoresis or ultrasound and bypassing the stratum corneum through microneedle arrays or ablation.

Molecular or chemical penetration enhancers provide an effective and inexpensive means of temporarily reducing skin resistance to the passage of actives and other molecules. Molecular penetration enhancers or 'MPE's' can enhance the diffusion of molecules across the skin by, for example, disrupting the lipid bilayers of the stratum corneum.

Over 300 substances have been identified as penetration enhancers but surprisingly few have been successfully developed into commercial formulations. Many potent enhancers are irritating to the cells of the epidermis which can limit both the choice and concentration of enhancers suitable for topical formulations.

Discovery of new MPE's to increase skin permeability is highly desireable and has been an area of high activity over the last 30 years. However, the number of substances identified to be penetration enhancers is still small relative to the more than 25,000,000 substances identified in the CAS registry (Chemical Abstracts Service, Columbus, Ohio, www.cas.org).

The number of candidate drugs suitable for topical and transdermal administration could be significantly increased with improved penetration enhancers.

SUMMARY OF THE INVENTION

It is an object of the present invention to provide a novel topical formulation.

It is another object of the present invention to provide a novel topical formulation for topical or transdermal administration of an active agent.

It is another object of the present invention to provide a topical formulation capable of providing improved fluxes of diclofenac (or a pharmaceutically acceptable salt thereof) through the skin as compared to the topical formulation taught by Sandborn.

Accordingly, in one of its aspects, the present invention provides a topical formulation comprising: (i) diclofenac or a pharmaceutically acceptable salt thereof, (ii) a first compound, and (iii) a second compound, wherein the first compound and second compound are different, and each is selected from the group consisting essentially of N-lauroyl sarcosine, sodium octyl sulfate, methyl laurate, isopropyl myristate, oleic acid, glyceryl oleate and sodium lauryl sulfoacetate.

In another of its aspects, the present invention provides a topical formulation comprising: (i) diclofenac or a pharmaceutically acceptable salt thereof, (ii) a first compound, (iii) a second compound, and (iv) a therapeutically acceptable carrier that is different from the first compound and the second compound, wherein the first compound and second compound are different, and each is selected from the group consisting essentially of N-lauroyl sarcosine, sodium octyl sulfate, methyl laurate, isopropyl myristate, oleic acid, glyceryl oleate and sodium lauryl sulfoacetate.

In yet another of its aspects, the present invention provides a topical formulation comprising diclofenac or a pharmaceutically acceptable salt thereof, a therapeutically acceptable carrier and a skin penetration enhancer, wherein the skin penetration enhancer consists essentially of a mixture of N-lauroyl sarcosine and oleic acid.

DETAILED DESCRIPTION OF THE PREFERRED EMBODIMENTS

The present invention provides a topical formulation that may be used for the topical or transdermal administration of at least one active agent. As used throughout this specification, the term 'transdermal', means in the broadest sense through the skin. Further the terms 'transdermal' and 'percutaneous' are used interchangeably throughout this specification.

As used herein the term 'topical formulation' refers to a formulation that may be applied to skin or a mucosa. Topical formulations may, for example, be used to confer therapeutic benefit to a patient or cosmetic benefits to a consumer. Topical formulations can be used for both topical and transdermal administration of substances.

The term 'topical administration' is used in its conventional sense to mean delivery of a substance, such as a therapeutically active agent, to the skin or a localized region of the body. Topical administration of a drug may often be advantageously applied in, for example, the treatment of various skin disorders.

The term 'transdermal administration' is used to mean administration through the skin. Transdermal administration is often applied where systemic delivery of an active is desired, although it may also be useful for delivering an active to tissues underlying the skin with minimal systemic absorption.

The term 'penetration enhancer' is used herein to refer to an agent that improves the transport of molecules such as an active agent (e.g., a medicine) into or through the skin. Various conditions may occur at different sites in the body either in the skin or below creating a need to target delivery of compounds. For example, in products designed to produce artificial tans delivery of dye substances into the stratum corneum may be advantageous. A psoriasis treatment on the other hand may require delivery of therapeutic drug levels in deeper epidermal tissue. In a treatment for osteoarthritis delivery of the active agent into deeper underlying joint tissue may be necessary to achieve therapeutic benefit. In yet other applications, for example in hormone replacement therapy, delivery of drug to the systemic circulation may be an objective. Thus, a 'penetration enhancer' may be used to assist in the delivery of an active agent directly to the skin or underlying tissue or indirectly to the site of the disease through systemic distribution. A penetration enhancer may be a pure substance or may comprise a mixture of different chemical entities. In this specification the terms 'penetration enhancer', 'chemical penetration enhancer', 'molecular penetration enhancer' and 'MPE' are used interchangeably.

As used herein the term 'multiplexed molecular penetration enhancers' means a penetration enhancer comprising two or more substances wherein each of the two or more substances is also penetration enhancer.

The present inventors have surprisingly and unexpectedly discovered that certain combination of compounds are excellent penetration enhancers and, as such, can be incorporated in a topical formulation to facilitate administration of diclofenac or a pharmaceutically acceptable salt thereof. The increased penetration enhancement can also lead to a reduction in the total concentration of skin irritants in the formulation.

The compounds acting as excellent penetration enhancers are used in combination—i.e., two (or more) compounds are selected from wherein the first compound and second compound are different, and each is selected from the group consisting essentially of N-lauroyl sarcosine, sodium octyl sulfate, methyl laurate, isopropyl myristate, oleic acid, glyceryl oleate and sodium lauryl sulfoacetate.

The preferred combinations of compounds that act as improved penetration enhancers include the following:
the first compound comprises N-lauroyl sarcosine and the second compound comprises isopropyl myristate;
the first compound comprises N-lauroyl sarcosine and the second compound comprises oleic acid;
the first compound comprises sodium octyl sulfate and the second compound comprises oleic acid;
the first compound comprises glyceryl oleate and the second compound comprises sodium octyl sulfate;
the first compound comprises glyceryl oleate and the second compound comprises methyl laurate;
the first compound comprises sodium lauryl sulfoacetate and the second compound comprises methyl laurate; and
the first compound comprises sodium lauryl sulfoacetate and the second compound comprises isopropyl myristate.

Preferably, the weight ratio of the first compound to the second compound is in the range of from about 1:9 to about 9:1. More preferably, the weight ratio of the first compound to the second compound is in the range of from about 1:4 to about 4:1. Even more preferably, the weight ratio of the first compound to the second compound is in the range of from about 1:3 to about 3:1. Even more preferably, the weight ratio of the first compound to the second compound is in the range of from about 1:2 to about 2:1. Most preferably, the weight ratio of the first compound to the second compound is about 1:1.

Preferably, the total concentration of the first compound and the second concentration is up to about 50 wt. % per unit volume of the formulation. More preferably, the total concentration of the first compound and the second concentration is up to about 40 wt. % per unit volume of the formulation. Even more preferably, the total concentration of the first compound and the second concentration is in the range of from about 1 to about to about 35 wt. % per unit volume of the formulation. Even more preferably, the total concentration of the first compound and the second concentration is in the range of from about 1 to about to about 30 wt. % per unit volume of the formulation. Even more preferably, the total concentration of We first compound and the second concentration is in the range of from about 1 to about to about 25 wt. % per unit volume of the formulation. Even more preferably, the total concentration of the first compound and the second concentration is in the range of from about 1 to about to about 20 wt. % per unit volume of the formulation. Even more preferably, the total concentration of the first compound and the second concentration is in the range of from about 1 to about to about 15 wt. % per unit volume of the formulation. Even more preferably, the total concentration of the first compound and the second concentration is in the range of from about 1 to about to about 10 wt. % per unit volume of the formulation. Even more preferably, the total concentration of the first compound and the second concentration is in the range of from about 1 to about to about 7.5 wt. % per unit volume of the formulation. Even more preferably, the total concentration of the first compound and the second concentration is in the range of from about 1 to about to about 5 wt. % per unit volume of the formulation.

Most preferably, the total concentration of the first compound and the second concentration is in the range of from about 2 to about to about 5 wt. % per unit volume of the formulation. Within this most preferred embodiment, it can, in some cases, be preferable to have the total concentration of the first compound and the second concentration in the range of from about 2 to about to about 4 wt. % per unit volume of the formulation.

The present topical formulation comprises diclofenac or a pharmaceutically acceptable salt thereof as a therapeutically active agent. A non-limiting example of such a pharmaceutically acceptable salt is diclofenac sodium.

The present topical formulation may also include one or more cosmetically or pharmaceutically acceptable carriers/excipients. Suitable carriers/excipients that may be used in the topical formulations discussed herein are known in the art and include, but are not limited to, solubilizers such as $C_2$ to $C_8$ straight and branched chain alcohols, diols and triols, moisturizers and humectants such as glycerine, amino acids and amino acid derivatives, polyaminoacids and derivatives, pyrrolidone carboxylic acids and its salts and derivatives, surfactants such as sodium laureth sulfate, sorbitan monolaurate, emulsifiers such as cetyl alcohol, stearyl alcohol, thickeners such as methyl cellulose, ethyl cellulose, hydroxymethylcellulose, hydroxypropylcellulose, polyvinylpyrollidone, polyvinyl alcohol and acrylic polymers. Other examples of suitable excipients, such as binders and fillers are listed in Remington's Pharmaceutical Sciences, 18th Edition, Ed. Alfonso Gennaro, Mack Publishing Co. Easton, Pa., 1995 and Handbook of Pharmaceutical Excipients, 3rd Edition, Ed. Arthur H. Kibbe, American Pharmaceutical Association, Washington D.C. 2000.

The topical formulation of the present invention may be formulated by those skilled in the art as liquids, solutions, emulsions, creams, lotions, suspensions, triturates, gels, jellies, foams, pastes, ointments, shampoos, adhesives and the like.

The penetration enhancing effect may be measured using techniques known in the art. An example of one measurement method is described in the Examples below.

The topical formulation described above may also include propylene glycol. The propylene glycol may be present in the formulation between about 1% to about 25% w/w. Additionally the topical formulation may also include ethanol and/or polyethylene glycol 300. The ethanol may be present in the formulation between about 1% to about 25% w/w. The polyethylene glycol 300 may be present in the range of between about 1% to about 80% w/w. In addition the topical formulation may include at least one moisturizer/humectant.

The present invention provides an improved topical formulation for preferably to facilitate topical or transdermal administration of diclofenac or a pharmaceutically acceptable salt thereof. This enhanced effect is discussed further below and illustrated in preferred embodiments of the invention described in the Examples.

The present topical formulation may be applied to the skin by any means known in the art including, but not limited to, by an aerosol, spray, pump-pack, brush, swab, or other applicator. Preferably, the applicator provides either a fixed or variable metered dose application such as a metered dose aerosol, a stored-energy metered dose pump or a manual metered dose pump. Preferably the drug delivery system is applied to the skin of the human or animal covering a delivery surface area between about 10 and 800 cm$^2$, more preferably between about 10 and 400 cm$^2$, and most preferably about 10 and 200 cm$^2$. The application is most preferably performed by means of a topical metered dose spray combined with an actuator nozzle shroud which together accurately control the amount and/or uniformity of the dose applied. One function of the shroud is to keep the nozzle at a pre-determined height above, and perpendicular to, the skin to which the drug delivery system is being applied. This function may also be achieved by means of a spacer-bar or the like. Another function of the shroud is to enclose the area above the skin in order to prevent or limit bounce-back and/or loss of the drug delivery system to the surrounding environment. Preferably the area of application defined by the shroud is substantially circular in shape.

The drug delivery system may be a unit volume dispenser with or without a roll-on or other type of applicator. It may also be necessary to apply a number of dosages on untreated skin to obtain the desired result.

Embodiments of the invention will be described with reference to the following Examples which are provided for illustrative purposes only and should not be used to limit the scope of or construe the invention.

EXAMPLES

A number of formulations (described in more detail below) containing diclofenac sodium (a non-steroidal anti-inflammatory drug or NSAID) were tested for permeation through porcine skin using Franz diffusion cells [as generally described in Franz T J: Percutaneous absorption. On the relevance of in vitro data. J Invest Dermatol 1975; 64:190-195].

More specifically, Franz cells with a 5 ml receptor well volume were used in conjunction with full-thickness porcine skin harvested at Perry Scientific (San Diego, Calif.). The porcine skin was shaved free of hair, washed with water and subcutaneous fat was removed. The donor well had an area of ~0.5 cm$^2$. Receptor wells were filled with isotonic phosphate buffered saline (PBS) doped with 0.01% sodium azide. The flanges of the Franz cell were coated with vacuum grease to ensure a complete seal and were clamped together with uniform pressure using a pinch clamp (SS #18 VWR 80073-350).

After the Franz cells were assembled, the porcine skin was allowed to pre-hydrate for 45 minutes with isotonic PBS. Isotonic PBS was then removed and 200 ml of the formulation was applied to the donor well. Receptor wells of the Franz cells were maintained at 37° C. (temperature on the surface of the skin is ~30° C.) in a stirring block with continual agitation via a stir bar.

The flux rates were calculated by assuming a radius of 0.4 cm in the donor well (i.e., an area of 0.503 cm$^2$). The HPLC calibration curve for diclofenac was determined to have a slope of 115.6 AUC/(µg diclofenac/ml).

Samples were drawn for from the receptor wells at t=24 hours and t=46 hours for all formulations. Franz diffusion cell measurements were made in five-fold replicates for each formulation.

The concentration of diclofenac in the samples was measured using HPLC analysis. Specifically, HPLC was carried out with C18 column and using acetonitrile and water as the mobile phase. Flux rates were calculated using standard equations based on the total transference of diclofenac across the skin after 46 hours. Thusk, flux rates, F, were computed according to $$F = \frac{D * V}{t * A},$$

wherein: D is the concentration of the drug in the receptor well after incubation time t, V is the volume of the receptor well and A is the surface area of skin.

Individual penetration enhancers in the Examples discussed below were obtained from the following sources:
glyceryl oleate (glycerol monooleate) from TCI (VWR), product code TCG0082
isopropyl myristate from Sigma product code M0757
methyl laurate from Chem Service product code CSO426
N-lauroyl sarcosine from Sigma product code L5000
oleic acid (octadecenoic acid) from Mallinckroft (VWR) product code MK274404
sodium lauryl sulfoacetate from Stepan (65-72%) product code Lathanol LAL
sodium octyl sulfate from Alfa Aesar (VWR) product code AA43750-06.

The base composition used for each formulation of a carrier composition comprising isotonic PBS, ethanol, propylene glycol and propylene glycol 300 in a volume ratio of 2:2:1:1. The base formulation further comprised diclofenac sodium in a concentration of 1.5 wt. % per unit volume of the base composition. In the Examples below, various combinations of skin penetration enhancing compounds detailed below were added to the base composition.

Example 1

In this Example, N-lauroyl sarcosine (NLS) and isopropyl myristate (IM) were added to the base formulation. The details of each formulation and the results of the Franz diffusion cell experiments are set out in Table 1.

With reference to Table, it can be seen that Formulation 2 (containing a mixture of NLS and IM each at a concentration 2.5% wt/vol.) was more effective at enhancing diclofenac sodium flux rates through the skin when compared to either of Formulation 3 (containing 5% wt./vol NLS and no IM) or Formulation 4 (containing 5% wt./vol IM and no NLS).

Further and surprisingly, Formulation 1 (containing a mixture of NLS and IM each at a concentration of 1.5% wt./vol) was approximately seven times more effective at enhancing the flux rate of the diclofenac sodium when compared to Formulation 2.

Example 2

In this Example, N-lauroyl sarcosine (NLS) and oleic acid (OA) were added to the base formulation. The details of each formulation and the results of the Franz diffusion cell experiments are set out in Table 2.

With reference to Table 2, it can be seen that Formulation 5 (containing a mixture of NLS and OA each at a concentration 1.5% wt/vol.) was more effective at enhancing diclofenac sodium flux rate through the skin when compared to either of Formulation 6 (containing 5% wt./vol NLS and no OA) or Formulation 7 (containing 5% wt./vol OA and no NLS).

It is notable that the flux rate of the NSAID in Formulation 5 was higher than that achieved by either of Formulation 6 or Formulation 7 in spite of the fact that the total concentration of the molecular penetration enhancers in Formulation 5 was lower that that in Formulation 6 and Formulation 7.

Example 3

In this Example, sodium octyl sulfate (SOS) and oleic acid (OA) were added to the base formulation. The details of each formulation and the results of the Franz diffusion cell experiments are set out in Table 3.

With reference to Table 3, it can be seen that Formulation 8 (containing a mixture of SOS and OA each at a concentration 1.5% wt/vol and 3.5% wt/vol, respectively) was more effective at enhancing diclofenac sodium flux rate through the skin when compared to either of Formulation 9 (containing 5% wt./vol OA and no SOS) or Formulation 10 (containing 5% wt./vol SOS and no OA).

Example 4

In this Example, glyceryl oleate (GO) and sodium octyl sulfate (SOS) were added to the base formulation. The details of each formulation and the results of the Franz diffusion cell experiments are set out in Table 4.

With reference to Table 4, it can be seen that Formulation 11 (containing a mixture of GO and SOS each at a concentration 1.5% wt/vol.) was approximately as effective at enhancing diclofenac sodium flux rate through the skin as Formulation 12 (containing 5% wt./vol GO and no SOS) and was substantially improved over that of Formulation 13 (containing 5% wt./vol SOS and no GO).

Example 5

In this Example, glyceryl oleate (GO) and methyl laurate (ML) were added to the base formulation. The details of each formulation and the results of the Franz diffusion cell experiments are set out in Table 5.

With reference to Table 5, it can be seen that Formulation 14 (containing a mixture of GO and ML each at a concentration 2.5% wt/vol.) was more effective at enhancing diclofenac sodium flux rate through the skin when compared to either of Formulation 15 (containing 5% wt./vol GO and no ML) or Formulation 16 (containing 5% wt./vol ML and no GO).

Example 6

In this Example, sodium lauryl sulfoacetate (SLSA) and methyl laurate (ML) were added to the base formulation. The details of each formulation and the results of the Franz diffusion cell experiments are set out in Table 6.

With reference to Table 6, it can be seen that Formulation 17 (containing a mixture of SLSA and ML each at a concentration 2.5% wt/vol.) was more effective at enhancing diclofenac sodium flux rate through the skin when compared to either of Formulation 18 (containing 5% wt./vol SLSA and no ML) or Formulation 19 (containing 5% wt./vol ML and no SLSA).

Example 7

In this Example, sodium lauryl sulfoacetate (SLSA) and isopropyl myristate (IM) were added to the base formulation. The details of each formulation and the results of the Franz diffusion cell experiments are set out in Table 7.

With reference to Table 7, it can be seen that Formulation 20 (containing a mixture of SLSA and IM each at a concentration 2.5% wt/vol.) was more effective at enhancing diclofenac sodium flux rate through the skin when compared to either of Formulation 21 (containing 5% wt./vol SLSA and no IM) or Formulation 22 (containing 5% wt./vol IM and no SLSA).

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. It is therefore contemplated that the appended claims will cover any such modifications or embodiments. Further, all of the claims are hereby incorporated by reference into the description of the preferred embodiments.

All publications, patents and patent applications referred to herein are incorporated by reference in their entirety to the same extent as if each individual publication, patent or patent application was specifically and individually indicated to be incorporated by reference in its entirety.

TABLE 1

| Formulation | [NLS + IM] (wt. %/vol.) | Weight Ratio of NLS:IM | Flux ($\mu$g/hr/cm$^2$) |
| --- | --- | --- | --- |
| 1 | 3.0 | 1:1 | 3.80 |
| 2 | 5.0 | 1:1 | 0.53 |
| 3 | 5.0 | 1:0 | 0.26 |
| 4 | 5.0 | 0:1 | 0.02 |

TABLE 2

| Formulation | [NLS + OA] (wt. %/vol.) | Weight Ratio of NLS:OA | Flux (μg/hr/cm²) |
|---|---|---|---|
| 5 | 3.0 | 1:1 | 3.29 |
| 6 | 5.0 | 1:0 | 0.26 |
| 7 | 5.0 | 0:1 | 2.70 |

TABLE 3

| Formulation | [SOS + OA] (wt. %/vol.) | Weight Ratio of SOS:OA | Flux (μg/hr/cm²) |
|---|---|---|---|
| 8 | 5.0 | 3:7 | 4.73 |
| 9 | 5.0 | 0:1 | 2.70 |
| 10 | 5.0 | 1:0 | 0.02 |

TABLE 4

| Formulation | [GO + SOS] (wt. %/vol.) | Weight Ratio of GO:SOS | Flux (μg/hr/cm²) |
|---|---|---|---|
| 11 | 3.0 | 1:1 | 0.30 |
| 12 | 5.0 | 1:0 | 0.34 |
| 13 | 5.0 | 0:1 | 0.02 |

TABLE 5

| Formulation | [GO + ML] (wt. %/vol.) | Weight Ratio of GO:ML | Flux (μg/hr/cm²) |
|---|---|---|---|
| 14 | 5.0 | 1:1 | 0.54 |
| 15 | 5.0 | 1:0 | 0.34 |
| 16 | 5.0 | 0:1 | 0.32 |

TABLE 6

| Formulation | [SLSA + ML] (wt. %/vol.) | Weight Ratio of SLSA:ML | Flux (μg/hr/cm²) |
|---|---|---|---|
| 17 | 5.0 | 3:7 | 0.52 |
| 18 | 5.0 | 1:0 | 0.22 |
| 19 | 5.0 | 0:1 | 0.32 |

TABLE 7

| Formulation | [SLSA + IM] (wt. %/vol.) | Weight Ratio of SLSA:IM | Flux (μg/hr/cm²) |
|---|---|---|---|
| 20 | 5.0 | 1:1 | 0.52 |
| 21 | 5.0 | 1:0 | 0.22 |
| 22 | 5.0 | 0:1 | 0.02 |

What is claimed is:

1. A topical formulation comprising:
   (i) diclofenac or a pharmaceutically acceptable salt thereof,
   (ii) a first compound, and
   (iii) a second compound,
   wherein the first compound and second compound are different, and each is selected from the group consisting of N-lauroyl sarcosine, sodium octyl sulfate, methyl laurate, isopropyl myristate, oleic acid, glyceryl oleate, and sodium lauryl sulfoacetate.

2. The topical formulation defined in claim 1, wherein the first compound comprises N-lauroyl sarcosine and the second compound comprises isopropyl myristate.

3. The topical formulation defined in claim 1, wherein the first compound comprises N-lauroyl sarcosine and the second compound comprises oleic acid.

4. The topical formulation defined in claim 1, wherein the first compound comprises sodium octyl sulfate and the second compound comprises oleic acid.

5. The topical formulation defined in claim 1, wherein the first compound comprises glyceryl oleate and the second compound comprises sodium octyl sulfate.

6. The topical formulation defined in claim 1, wherein the first compound comprises glyceryl oleate and the second compound comprises methyl laurate.

7. The topical formulation defined in claim 1, wherein the first compound comprises sodium lauryl sulfoacetate and the second compound comprises methyl laurate.

8. The topical formulation defined in claim 1, wherein the first compound comprises sodium lauryl sulfoacetate and the second compound comprises isopropyl myristate.

9. The topical formulation defined in claim 1, further comprising at least one biologically acceptable excipient.

10. The topical formulation defined in claim 1, wherein the total concentration of the first compound and the second concentration is up to about 50 wt. % per unit volume of the formulation.

11. The topical formulation defined in claim 1, wherein the total concentration of the first compound and the second concentration is up to about 40 wt. % per unit volume of the formulation.

12. The topical formulation defined in claim 1, wherein the total concentration of the first compound and the second concentration is in the range of from about 1 to about to about 35 wt. % per unit volume of the formulation.

13. The topical formulation defined in claim 1, wherein the total concentration of the first compound and the second concentration is in the range of from about 1 to about to about 30 wt. % per unit volume of the formulation.

14. The topical formulation defined in claim 1, wherein the total concentration of the first compound and the second concentration is in the range of from about 1 to about to about 25 wt. % per unit volume of the formulation.

15. The topical formulation defined in claim 1, wherein the total concentration of the first compound and the second concentration is in the range of from about 1 to about to about 20 wt. % per unit volume of the formulation.

16. The topical formulation defined in claim 1, wherein the total concentration of the first compound and the second concentration is in the range of from about 1 to about to about 15 wt. % per unit volume of the formulation.

17. The topical formulation defined in claim 1, wherein the total concentration of the first compound and the second concentration is in the range of from about 1 to about to about 10 wt. % per unit volume of the formulation.

18. The topical formulation defined in claim 1, wherein the total concentration of the first compound and the second concentration is in the range of from about 1 to about to about 7.5 wt. % per unit volume of the formulation.

19. The topical formulation defined in claim 1, wherein the total concentration of the first compound and the second concentration is in the range of from about 1 to about to about 5 wt. % per unit volume of the formulation.

20. The topical formulation defined in claim 1, wherein the total concentration of the first compound and the second concentration is in the range of from about 2 to about to about 5 wt. % per unit volume of the formulation.

21. The topical formulation defined in claim 1, wherein the total concentration of the first compound and the second concentration is in the range of from about 2 to about to about 4 wt. % per unit volume of the formulation.

22. The topical formulation defined in claim 1, wherein the weight ratio of the first compound to the second compound is in the range of from about 1:9 to about 9:1.

23. The topical formulation defined in claim 1, wherein the weight ratio of the first compound to the second compound is in the range of from about 1:4 to about 4:1.

24. The topical formulation defined in claim 1, wherein the weight ratio of the first compound to the second compound is in the range of from about 1:3 to about 3:1.

25. The topical formulation defined in claim 1, wherein the weight ratio of the first compound to the second compound is in the range of from about 1:2 to about 2:1.

26. The topical formulation defined in claim 1, wherein the weight ratio of the first compound to the second compound is about 1:1.

27. A topical formulation comprising:
diclofenac or a pharmaceutically acceptable salt thereof,
a therapeutically acceptable carrier, and
a skin penetration enhancer,
wherein the skin penetration enhancer consists essentially of a mixture of N-lauroyl sarcosine and oleic acid.

28. The topical formulation defined in claim 27, wherein the weight ratio of N-lauroyl sarcosine to oleic acid is in the range of from about 1:3 to about 3:1.

29. The topical formulation defined in claim 27, wherein the weight ratio of N-lauroyl sarcosine to oleic acid is in the range of from about 1:2 to about 2:1.

30. The topical formulation defined in claim 27, wherein the weight ratio of N-lauroyl sarcosine to oleic acid is about 1:1.

31. The topical formulation defined in claim 27, wherein the total concentration of N-lauroyl sarcosine and oleic acid is in the range of from about 2 to about to about 5 wt. % per unit volume of the formulation.

32. The topical formulation defined in claim 27, wherein the total concentration of N-lauroyl sarcosine and oleic acid is in the range of from about 2 to about to about 4 wt. % per unit volume of the formulation.

33. The topical formulation defined in claim 27, wherein the total concentration of N-lauroyl sarcosine and oleic acid is 3 wt. % per unit volume of the formulation.

* * * * *

UNITED STATES PATENT AND TRADEMARK OFFICE
CERTIFICATE OF CORRECTION

PATENT NO.         : 7,795,309 B2
APPLICATION NO.    : 12/281561
DATED              : September 14, 2010
INVENTOR(S)        : Kisak et al.

Page 1 of 1

It is certified that error appears in the above-identified patent and that said Letters Patent is hereby corrected as shown below:

1. Column 3, line 42, "also penetration" should read -- also a penetration --.
2. Column 3, line 44, "combination" should read -- combinations --.
3. Column 4, lines 26, 29, 32, 35, 38, 42, 45, 48, 52, 56, "to about to about" should read -- to about --.
4. Column 4, lines 20, 22, 25, 28, 31, 34, 38, 41, 44, 47, 51, 55, "concentration" should read -- compound --.
5. Column 4, line 31, "We" should read -- the --.
6. Column 5, line 33, "for" should read -- , --.
7. Column 5, line 47, "preferably about" should read -- preferably between about --.
8. Column 6, line 24, "C." should read -- C --.
9. Column 6, line 31, "drawn for" should read -- drawn --.
10. Column 6, line 40, "Thusk" should read -- Thus --.
11. Column 7, line 12, "Table," should read -- Table 1, --.
12. Column 10, lines 26, 30, 34, 38, 42, 46, 50, 54, 58, 62 and 66, "concentration" should read -- compound --.
13. Column 10, lines 34, 38, 42, 46, 50, 54, 58, 62, 66 and column 11, line 3, "to about to about" should read -- to about --.
14. Column 11, line 3, "concentration" should read -- compound --.
15. Column 12, lines 14 and 18, "to about to about" should read -- to about --.

Signed and Sealed this
Sixth Day of December, 2011

David J. Kappos
*Director of the United States Patent and Trademark Office*